US005789201A

United States Patent [19]
Guastella

[11] Patent Number: 5,789,201
[45] Date of Patent: Aug. 4, 1998

[54] GENES CODING FOR BCL-Y A BCL-2 HOMOLOGUE

[75] Inventor: John Guastella, Irvine, Calif.

[73] Assignee: CoCensys, Inc., Irvine, Calif.

[21] Appl. No.: 798,897

[22] Filed: Feb. 11, 1997

Related U.S. Application Data

[60] Provisional application No. 60/012,201 Feb. 23, 1996.

[51] Int. Cl.$^6$ .................... C12P 21/06; C07H 21/04; C12N 5/00
[52] U.S. Cl. .................. 435/69.1; 435/325; 435/252.3; 435/70.1; 435/320.1; 536/23.5; 530/350
[58] Field of Search .................... 536/23.5; 435/325, 435/252.3, 320.1, 70.1, 69.1; 530/350

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,965,188 | 10/1990 | Mullis et al. | 435/6 |
| 5,015,568 | 5/1991 | Tsujimoto et al. | 435/5 |
| 5,399,346 | 3/1995 | Anderson et al. | 424/93.21 |
| 5,523,393 | 6/1996 | Tsujimoto et al. | 530/350 |
| 5,622,852 | 4/1997 | Korsmeyer | 435/325 |
| 5,641,672 | 6/1997 | Dalla-Favera et al. | 435/325 |
| 5,646,008 | 7/1997 | Thompson et al. | 435/69.1 |

FOREIGN PATENT DOCUMENTS

| | | |
|---|---|---|
| WO 95/00160 | 1/1995 | WIPO. |
| WO 95/13292 | 5/1995 | WIPO. |
| WO 96/38569 | 12/1996 | WIPO. |

OTHER PUBLICATIONS

Guastella, J. et al. Soc. Neuro Sci. Abstract 21 (1–3): 1067, 1995.

Benoist, C., and Chambon, P., "In vivo sequence requirements of the SV40 early promoter region," *Nature* 290:304–310 (1981).

Bollon, A.P., and Stauver, M., "DNA Transformation Efficiency of Various Bacterial and Yeast Host–Vector Systems," *J. Clin. Hematol. Oncol.* 10:39–48 (1980).

Broach, J.R., "The Yeast Plasmid 2μ Circle," *Cell* 28:203–204 (1982).

Cotten, M., et al., "Transferrin–polycation–mediated introduction of DNA into human leukemic cells: Stimulation by agents that affect the survival of transfected DNA or modulate transferrin receptor levels," *Proc. Natl. Acad. Sci. USA* 87:4033–4037 (1990).

Cotten, M., et al., "High–efficiency receptor–mediated delivery of small and large (48 kilobase gene constructs using the endosome–disruption activity of defective or chemically inactivated adenovirus particles," *Proc. Natl. Acad. Sci. USA* 89:6094–6098 (1992).

Curiel, D.T., et al., "Adenovirus enhancement of transferrin–polylysine–mediated gene delivery," *Proc. Natl. Acad. Sci. USA* 88:8850–8854 (1991).

Curiel, D.T., et al., "Gene Transfer to Respiratory Epithelial Cells via the Receptor–mediated Endocytosis Pathway," *Am. J. Respir. Cell Mol. Biol.* 6:247–252 (1992).

Curiel, T.J., et al., "Foreign Gene Expression in EBV–Transformed B–Cells: Potential for the Development of Novel CTL Target Cells," *J. Cell. Biochem. Suppl.* 60:Q407 (1992).

Davies, A.M., "The Bcl–2 family of proteins, and the regulation of neuronal survival," *Trends Neurosci.* 18:355–358 (Aug. 1995).

Gibson, L., et al., "bcl–w, a novel member of the bcl–2 family, promotes cell survival," *Oncogene* 13:665–675 (Aug. 1996).

Hamer, D.H., and Walling, M., "Regulation In Vivo of a Cloned Mammalian Gene: Cadmium Induces the Transcription of a Mouse Metallothionein Gene in SV40 Vectors," *J. Mol. Appl. Genet.* 1:273–288 (1982).

Johnston, S.A., and Hopper, J.E., "Isolation of the yeast regulatory gene GAL4 and analysis of its dosage effects on the galactose/melibiose regulon," *Proc. Natl. Acad. Sci. USA* 79:6971–6975 (1982).

Leary, J.J., et al., "Rapid and sensitive colorimetric method for visualizing biotin–labeled DNA probes hybridized to DNA or RNA immobilized on nitrocellulos: Bio–blots," *Proc. Natl. Acad. Sci. USA* 80:4045–4049 (1983).

Leff, D.N., "Future Gene Therapy For Spinal Cord Injury Regrows Severed Axons In Transgenic Mice," *BioWorld Today* 8:1,5 (Jan. 1997).

Levi–Schaffer, F., et al., "Coculture of interleukin 3–dependent mouse mast cells with fibroblasts results in a phenotypic change of the mast cells," *Proc. Natl. Acad. Sci. USA* 83:6485–6488 (1986).

Lichtenstein, C., "Anti–sense RNA as a tool to study plant gene expression," *Nature* 333:801–802 (1988).

McKnight, S.L., "Functional Relationships between Transcriptional Control Signals of the Thymidine Kinase Gene of Herpes Simplex Virus," *Cell* 31:355–365 (1982).

Razin, E., et al., "Interleukin 3: A Differentiation and Growth Factor for the Mouse Mast Cell that Contains Chondroitin Sulfate E Proteoglycan," *J. Immunol.* 132:1479–1486 (1984).

Renz, M., "Polynucleotide–histone H1 complexes as probes for blot hybridization," *EMBO J.* 2:817–822 (1983).

Renz, M., and Kurz, C., "A colorimetric method for DNA hybridization," *Nucl. Acids Res.* 12:3435–3444 (1984).

Reynolds, D.S., et al., "Immortalization of Murine Connective Tissue–type Mast Cells at Multiple Stages of Their Differentiation by Coculture of Splenocytes with Fibroblasts That Produce Kirsten Sarcoma Virus," *J. Biol. Chem.* 263:12783–12791 (1988).

(List continued on next page.)

*Primary Examiner*—Lila Feisee
*Assistant Examiner*—Minh-Fam Davis
*Attorney, Agent, or Firm*—Sterne, Kessler, Goldstein & Fox P.L.L.C.

[57] ABSTRACT

Mammalian genes coding for bcl-y are disclosed. Bcl-y is involved in mediating cell death or survival.

8 Claims, 3 Drawing Sheets

OTHER PUBLICATIONS

Rigby, P.W.J., et al., "Labeling Deoxyribonucleic Acid to High Specific Activity in Vitro by Nick Translation with DNA Polymerase I," *J. Mol. Biol.* 113:237–251 (1977).

Silver, P.A., et al., "Amino terminus of the yeast GAL4 gene product is sufficient for nuclear localization," *Proc. Natl. Acad. Sci. USA* 81:5951–5955 (1984).

Wagner, E., et al., "Transferrin–polycation–DNA complexes: The effect of polycations on the structure of the complex and DNA delivery to cells," *Proc. Natl. Acad. Sci. USA* 88:4255–4259 (1991).

Wagner, E., et al., "DNA–Binding Transferrin Conjugates as Functional Gene–Delivery Agents: Synthesis by Linkage of Polylysine or Ethidium Homodimer to the Transferrin Carbohydrate Moiety," *Bioconjugate Chem.* 2:226–231 (1991).

```
RBCLY      MATPASTP-DTRALVADFVGYKLRQKGYV------------------------------        28
HBCLY      MATPASAP-DTRALVEDFVGYKLRQKGYV------------------------------        28
HUMBCL2A   MAHAGRTGYDNREIVMKYIHYKLSQRGYEWDAGDVGAAPPGAAPAPGIFS                  50
HUMBCLXL   MSQS------NRELVVDFLSYKLSQKGYSWSQFSDVEENRTEAPEGTESE                  44
HUMBAXA    MDGSG-----------------------------EQPRGGGPTSSEQI                   19
             *.

RBCLY      -----------------------------CGAGPGEGPAADPLHQAMRAA                 49
HBCLY      -----------------------------CGAGPGEGPAADPLHQAMRAA                 49
HUMBCL2A   SQPGHTPHPAASRDPVARTSPLQTPAAPGAAAGPALSPVPPVVHLALRQA                 100
HUMBCLXL   METPSAINGNPSWHLADSPAVNGATGHSSSLDAREVIPMAAVKQ-ALREA                 93
HUMBAXA    MKTGALLLQGF----IQDRAGRMGGEAPELALDPVPQDASTKKLSECLKRI                66
                                  :

RBCLY      GDEFETRFRRTFSDLAAQLHVTPGSAQQRFTQVSDELFQGGP-NWGRLVA                  98
HBCLY      GDEFETRFRRTFSDLAAQLHVTPGSAQQRFTQVSDELFQGGP-NWGRLVA                  98
HUMBCL2A   GDDFSRRYRGDFAEMSSQLHLTPFTARGRFATVVEELFRDGV-NWGRIVA                  149
HUMBCLXL   GDEFELRYRRAFSDLTSQLHITPGTAYQSFEQVVNELFRDGV-NWGRIVA                  142
HUMBAXA    GDELDS---NMELQRMIAA---VDTDSPREVFFRVAADMFSDGNFNWGRVVA                112
           **.                     .   *   ..:.*   .*   ****.**

RBCLY      FFVFGAALCAESVNKEMEPLVGQVQDWMVTYLETRLADWIHSSGGWAEFT                  148
HBCLY      FFVFGAALCAESVNKEMEPLVGQVQEWMVAYLETRLADWIHSSGGWAEFT                  148
HUMBCL2A   FFEFGGVMCVESVNREMSPLVDNIALWMTEYLNRHLHTWIQDNGGWDAFV                  199
HUMBCLXL   FSSFGGALCVESVDKEMQVLVSRIAAWMATYLNDHLEPWIQENGGWDTFV                  192
HUMBAXA    LFYFASKLVLKALCTKVPELIRTIMGWTLDFLRERLLGWIQDQGGWDGLL                  162
           .*.*      *.:*  .*  ..** .*  *.    ..* .*** ** **

RBCLY      ALYGDGALEEARR--LREGNWASVRTVLTGAVALGALVTVGAFFASK                     193
HBCLY      ALYGDGALEEARR--LREGNWASVRTVLTGAVALGALVTVGAFFASK                     193
HUMBCL2A   ELYGP-----SMRPLFDFSWLSIKTLLSLAL-VGACITLGAYLSHK                      239
HUMBCLXL   ELYGNNAAAESRKGQERFNRWFLTGM----T-VAGVVLGSLFSRK                       233
HUMBAXA    SYFGTPT-------------WQTVTIFVAGVLTAS----LTIWKKMG                     192
             .*                :   .    .        ..

| | | | | | | | | | | | | | | | | | | | |
|---|---|---|---|---|---|---|---|---|---|---|---|---|---|---|---|---|---|---|---|
| bcl-y | E | L | F | Q | G | G | P | - | N | W | G | R | L | V | A | F | F | V | F G A |
| bcl-2 | E | L | F | R | D | G | V | - | N | W | G | R | I | V | A | F | F | E | F G G |
| BAX | D | M | F | S | D | G | N | F | N | W | G | R | V | V | A | L | F | Y | F A S |
| bcl-x | E | L | F | R | D | G | V | - | N | W | G | R | I | V | A | F | F | S | F G G |
| MCL1 | H | V | F | S | D | G | V | T | N | W | G | R | I | V | T | L | I | S | F G A |
| A1 | K | E | F | E | D | G | I | I | N | W | G | R | I | V | T | I | F | A | F G G |
| ced-9 | A | Q | T | D | Q | C | P | M | S | Y | G | R | L | I | G | L | I | S | F G G |

| | | | | | | | | | | | | | |
|---|---|---|---|---|---|---|---|---|---|---|---|---|---|
| bcl-y | D | W | I | H | S | S | G | G | W | A | E | F | T A L Y |
| bcl-2 | T | W | I | Q | D | N | G | G | W | D | A | F | V E L Y |
| BAX | G | W | I | Q | D | Q | G | G | W | D | G | L | L S Y F |
| bcl-x | P | W | I | Q | E | N | G | G | W | D | T | F | V E L Y |
| MCL1 | D | W | L | V | K | Q | R | G | W | D | G | F | V E F F |
| A1 | E | W | I | R | Q | N | G | G | W | E | D | G | F I K K |
| ced-9 | N | W | K | E | H | N | R | S | W | D | D | F | M T L G |

Figure 3C

| | | | | | | | | | | | | | | | | | |
|---|---|---|---|---|---|---|---|---|---|---|---|---|---|---|---|---|---|
| I | L | A | T | V | A | A | T | - | - | G | - | - | - | T | A | I G A Y | Mas70p |
| L | L | - | S | L | A | L | V | - | - | G | A | C | I | T | - | L G A Y | hbcl-2 |
| V | L | - | T | G | A | V | A | L | - | G | A | L | V | T | - | V G A F | hbcl-y |
| W | F | L | T | G | M | T | V | - | - | A | G | V | V | L | L | G S L | hbcl-x |

Figure 3D

GENES CODING FOR BCL-Y A BCL-2 HOMOLOGUE

CROSS REFERENCE TO RELATED APPLICATIONS

This application claims priority to U.S. provisional application Ser. No. 60/012,201 filed Feb. 23, 1996.

BACKGROUND OF THE INVENTION

1. Field of the Invention

The present invention is in the field of recombinant genetics.

2. Related Art

The mechanism of cell death has come under increasing scrutiny in the last few years as scientists have sought to understand the biological basis of this phenomenon. Recent studies have shown that, in many cases, cell death is an active process involving a complex network of death triggers, death regulators and death effectors. The interactions of these death factors produce cell death pathways whose characteristics are really no different in principle from the pathways of intermediary metabolism. This realization has opened up the "black box" of cell death, allowing physiologists, biochemists and geneticists to begin to delineate cell death pathways and to identify the molecules involved.

Classically, two distinct forms of cell death have been recognized: necrosis and apoptosis. These processes have been distinguished based mostly on morphological criteria. In necrosis, cell and organelle swelling is a notable feature and the cells eventually burst releasing their contents into the surrounding tissue space. By contrast, the hallmark of apoptosis is cell shrinkage and organelle changes are uncommon. The exception to this is the nucleus where the chromatin condenses and becomes redistributed just under the nuclear envelope. Rather than bursting, apoptotic cells break up into small parcels containing plasma membrane, cytosol, organelles and pieces of nucleus. These so-called "apoptotic bodies" are eventually phagocytosed by neighboring cells, and can be visualized histochemically. Another important attribute of apoptosis (and the only established biochemical marker) is the discrete degradation of DNA resulting in a characteristic "DNA ladder" when analyzed on DNA-separating gels. These features (cell swelling vs. cell shrinkage and DNA ladder formation) have been used to characterize the death process in a variety of in vitro and in vivo models of cell death. However, it is important to realize that, although necrosis and apoptosis are still discussed in the literature as being distinct entities, they may, in fact, represent the extremes of a continuum of cell death processes and might share certain molecular features.

There are profound clinical implications to understanding the biology of cell death. In the normal development of a multicellular organism, many more cells are produced than are needed in the mature or adult tissue. Therefore, the process of cell birth (mitosis) must be counterbalanced by a process for reducing cell number. Obviously, if this homeostatic mechanism is disturbed, cells will die when they shouldn't and will live when they should die. There is a tremendous range of diseases in which a disruption of the normal cell death pathway may therefore play a central role. In nervous system disorders such as stroke and head trauma, neurons die due to external death triggers such as a lack of oxygen or excess excitatory neurotransmitters. Recent studies suggest that at least a portion of this neuronal death may occur by an apoptotic mechanism. In other neural diseases, such as Alzheimer's disease, and amyotrophic lateral sclerosis, neurons die as part of a degenerative process whose triggers have not yet been determined, but which could possibly involve apoptosis. By contrast, in disorders such as cancer and hyperimmune diseases, cells live when they should, die, resulting in tumors (cancer) or an overactive immune system (autoimmune diseases). Thus, the ability to intervene pharmacologically in the cell death pathway may provide a completely new set of therapeutic agents useful in a wide range of human diseases.

Several gene families have been implicated as critical players in the cell death pathway. One of the most interesting of these gene families is the bcl-2/ced-9 family. The first member of this family, bcl-2, was initially identified as a causal factor in certain types of lymphatic cancer (B-cell lymphoma, hence the name). In this disorder, bcl-2 is overexpressed resulting in an abnormally longer lifespan for B-cells which allows these cells to accumulate additional mutations resulting in frank malignancy and lymphatic tumor development. Since being identified, the bcl-2 gene and its protein product have been intensively studied and found to be an effective blocker of both necrotic and apoptotic cell death in several model systems, including models of nerve cell death. The biochemical function of bcl-2 is not known (i.e., it is not clear whether it acts as an enzyme, receptor or signaling molecule). However, some experiments suggest that bcl-2 may play a role in cellular antioxidant pathways. This antioxidant theory of bcl-2 action is bolstered by the finding that the bcl-2 protein is localized to intracellular membranes, including mitochondria, an organelle thought to participate in the production of toxic oxygen radicals. However, it should be kept in mind that some experiments suggest that bcl-2 can block cell death even under conditions when oxygen radical-inducing death does not occur, suggesting that there may be several parallel pathways of cell death, with bcl-2 having the ability to block several of these pathways.

Since the discovery of bcl-2, nine other genes structurally related to it have been discovered (see Table 1). These genes include ced-9, a bcl-2 homologue found in the worm, *C. elegans*, and several related genes expressed in viruses. The existence of this gene family suggests that a group of bcl-2-like molecules function within the cell to control cell viability. Interestingly, not all bcl-2 family members block cell death. Instead, some seem to promote cell death. In addition, some members of the family can bind to other members of the family, and this interaction appears to regulate the cell death pathway. These findings have led to the hypothesis that the bcl-2 family members form part of a combinatorial mechanism. In this model, the interaction of family members with each other, and possibly with unrelated proteins, can determine whether a cell will live or die.

For a recent review of the bcl-2 family of proteins, reference is made to Davies, A. H., *Trends Neuroscience* 18:355–358 (1995). See also WO95/13292, WO95/00160 and U.S. Pat. No. 5,015,568.

Because of the importance of the bcl-2 family in controlling cell death, a PCR-based cloning strategy was employed to identify new members of this family with particular emphasis on finding bcl-2 homologues which are enriched in the brain. The present invention is directed to the molecular cloning and analysis of one such homologue, which is designated bcl-y.

SUMMARY OF THE INVENTION

The present invention relates to a gene coding for mammalian bcl-y.

The invention also relates to a vector containing the gene of the invention, as well as cellular hosts transformed with such vectors.

The invention also relates to substantially pure mammalian bcl-y protein.

The invention also relates to a method of preparing mammalian bcl-y protein, comprising:

(a) obtaining a cellular host transformed with a vector containing a gene coding for mammalian bcl-y;

(b) cultivating said host under conditions which result in the expression of mammalian bcl-y;

(c) isolating the mammalian bcl-y protein so expressed.

The present invention also relates to antisense RNA that is capable of hybridizing to bcl-y encoding mRNA.

BRIEF DESCRIPTION OF THE FIGURES

FIG. 2 shows the alignment of the rat and human bcl-y proteins (SEQ ID NOs: 3, 4) with the human bcl-2 (SEQ ID NOs: 11–14), bcl-x (SEQ ID NOs: 15–19), and BAX (SEQ ID NOs: 20–26) proteins. Identical residues are marked with an asterisk, and similar residues are marked by a dot.

FIG. 3A shows the amino acid sequence of rat bcl-y (SEQ ID NO:3).

FIG. 3B shows BH1 of rat and human bcl-y (SEQ ID NOs: 27 and 28) aligned with comparable regions from other bcl-2 family members (SEQ ID NOs: 29–36).

FIG. 3C shows BH2 of rat and human bcl-y (SEQ ID NO:37)aligned with comparable regions from other bcl-2 family members (SEQ ID NOs: 38–43).

FIG. 3D shows the putative C-terminal mitochondrial membrane anchor domain of bcl-y (SEQ ID NOs: 44–46) aligned with comparable regions of bcl-2 (SEQ ID NOs: 47–49), bcl-x (SEQ ID NOs: 50 and 51) and Mas70p, a yeast protein known to be located at the outer mitochondrial membrane (SEQ ID NOs: 52 and 53).

TABLE LEGENDS

Figure 1:
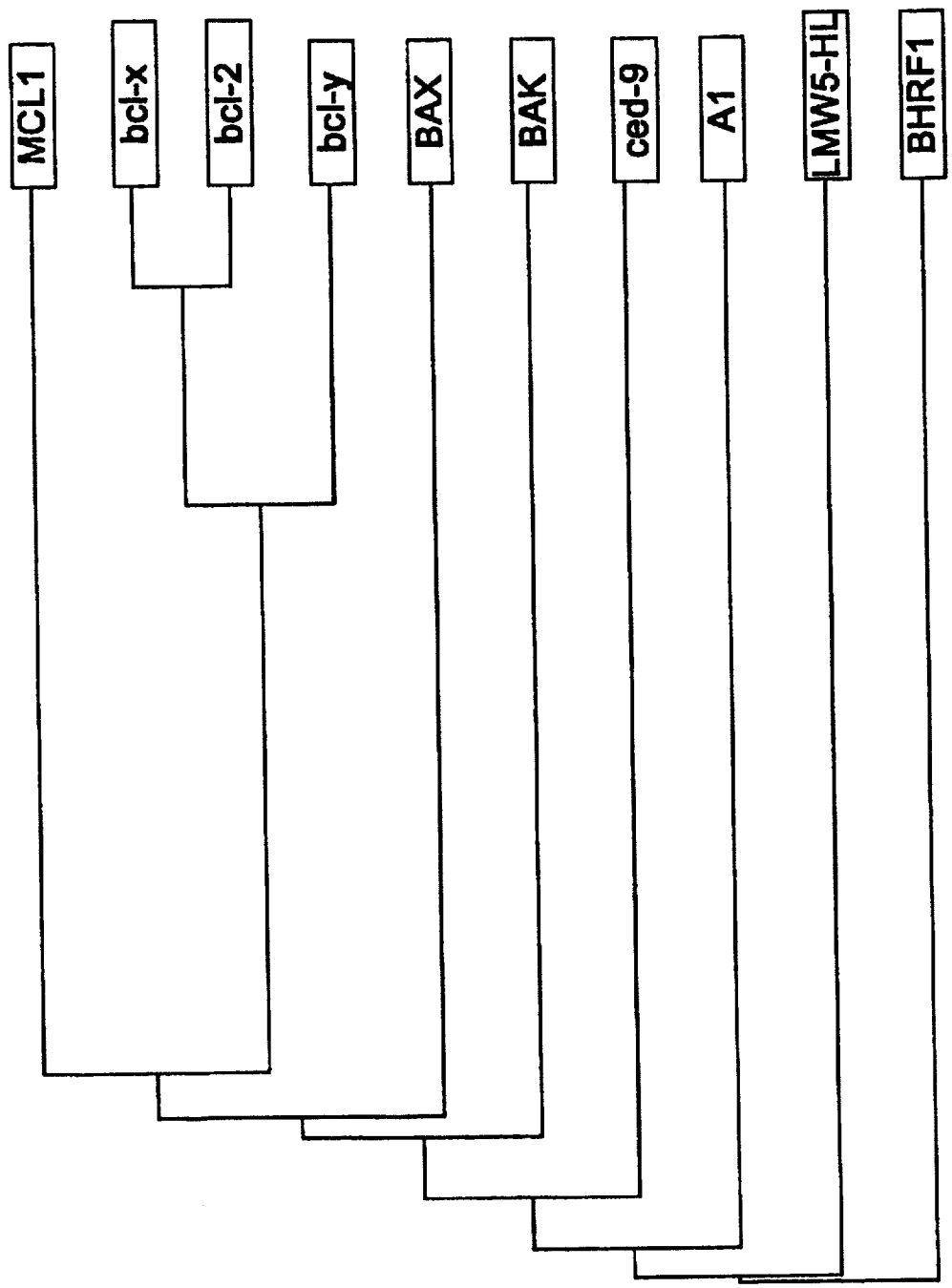
FIG. 1 is a dendrogram showing the sequence relationship at the amino acid level between bcl-y and other members of the bcl-2 family.

Table 1. List of known bcl-2 family members (except for bcl-y), their effect on cell viability (if known) and their tissue distribution.

Table 2. Percent homologies between bcl-y and bcl-x, bcl-2, BAX and MCL1. The data are expressed as % identity/% similarity.

Table 3. List of bcl-y expression constructs made so far.

DETAILED DESCRIPTION OF THE PREFERRED EMBODIMENTS

The invention is thus directed to genomic or cDNA having sequences which encode mammalian bcl-y. The invention also provides for cloning vectors and expression vectors containing such sequences, host cells transformed with such cloning vectors and expression vectors, the recombinant nucleic acid or proteins made in such host/ vectors systems and the functional derivatives of these recombinant proteins. The use of the isolated genes or proteins for the purpose promoting or inhibiting cell death is also part of the invention.

The invention is also directed to methods for controlling the programmed death of vertebrate cells by regulating the activity of bcl-y. Such regulation may take the form of inhibiting the activity of bcl-y, e.g. through the use of antisense oligonucleotides in order to prevent cell death. In this way, it may be possible to develop cell lines which remain viable in culture for an extended period of time or indefinitely. Certain cells can only be maintained in culture if they are grown in the presence of growth factors. By blocking cell death, it may be possible to make such cells growth factor independent. Alternatively, the expression of bcl-y may be increased in order to promote cell death. Such increased activity may be used in cancer cells to antagonize the effect of oncogenes.

In the description that follows, a number of terms used in recombinant DNA (rDNA) technology or in the research area of programmed cell death are extensively utilized. In order to provide a clear and consistent understanding of the specification and claims, including the scope to be given such terms, the following definitions are provided.

Gene. A DNA sequence containing a template for an RNA polymerase. The RNA transcribed from a gene may or may not code for a protein. RNA that codes for a protein is termed messenger RNA (mRNA).

A "complementary DNA" or "cDNA" gene includes recombinant genes synthesized by reverse transcription of mRNA and from which intervening sequences (introns) have been removed.

Cloning vector. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vector may further contain a marker suitable for use in the identification of cells transformed with the cloning vehicle. Markers, for example, are tetracycline resistance or ampicillin resistance. The term "cloning vehicle" is sometimes used for "cloning vector."

Expression vector. A vector similar to a cloning vector but which is capable of expressing a gene which has been cloned into it, after transformation into a host. The cloned gene is usually placed under the control of (i.e., operably linked to) certain control sequences such as promoter sequences. Control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Promoter. A DNA sequence generally described as the 5'-region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. Numerous promoters are well known to those of ordinary skill in the art and can be used in the practice of the invention.

Programmed cell death. The process in which cell death is genetically programmed. Programmed cell death allows organisms to get rid of cells that have served a developmental purpose but which are no longer beneficial.

Functional Derivative. A "functional derivative" of such as bcl-2 is a protein which possesses a biological activity that is substantially similar to the biological activity of such as bcl-2. A functional derivative of may or may not contain post-translational modifications such as covalently linked carbohydrate, depending on the necessity of such modifications for the performance of a specific function. The term "functional derivative" is intended to include the "fragments," "variants," "analogues," or "chemical derivatives" of a molecule.

Fragment. A "fragment" is meant to refer to any variant of the molecule, such as the peptide core, or a variant of the peptide core.

As deduced from the DNA sequence (SEQ ID NOs: 1 and 2), the rat and human bcl-2 proteins are 193 amino acids in length (including methionine at position 1). The amino acid sequence of the rat bcl-y protein is shown in SEQ ID NO:3 and the human bcl-y protein is shown is SEQ ID NO:4.

Genes coding for bcl-y preferably may be prepared by PCR using primers described herein according to Mullis, U.S. Pat. Nos. 4,683,195, 4,683,202 and 4,965,188.

Genomic DNA can be extracted and purified from any cell containing the particular mammalian chromosomes by means well known in the art (for example, see *Guide to Molecular Cloning Techniques*, S. L. Berger et al., eds., Academic Press (1987)). Alternatively, mRNA can be isolated from any cell which expresses the genes, and used to produce cDNA by means well known in the art (Id.). The mRNA coding for the protein may be enriched by techniques commonly used to enrich mRNA preparations for specific sequences, such as sucrose gradient centrifugation.

For cloning into a vector, DNA prepared as described above (either genomic DNA or preferably cDNA) is randomly sheared or enzymatically cleaved, and ligated into appropriate vectors to form a recombinant gene library. A DNA sequence encoding the protein or its functional derivatives may be inserted into a DNA vector in accordance with conventional techniques. Techniques for such manipulations are disclosed by Sambrook, et al., supra, and are well known in the art.

In a preferred method, oligonucleotide probes specific for the gene are designed from the cDNA sequences shown in SEQ ID NOs: 1 and 2. The oligonucleotide may be synthesized by means well known in the art (see, for example, *Synthesis and Application of DNA and RNA*, S. A. Narang, ed., 1987, Academic Press, San Diego, Calif.) and employed as a probe to identify and isolate the cloned gene by techniques known in the art. Techniques of nucleic acid hybridization and clone identification are disclosed by Maniatis, T., et al. (In: *Molecular Cloning, A Laboratory Manual*, Cold Spring Harbor Laboratories, Cold Spring Harbor, N.Y. (1982)), and by Hames, B. D., et al. (In: *Nucleic Acid Hybridization, A Practical Approach*, IRL Press, Washington, D.C. (1985)). Those members of the above-described gene library which are found to be capable of such hybridization are then analyzed to determine the extent and nature of the coding sequences which they contain.

It will be appreciated that trivial variations in the disclosed sequences and fragments derived from the full-length genomic and cDNA genes are encompassed by the invention as well. In particular, the invention relates to the mammalian genes coding for bcl-y that have at least 85 % sequence identity with the nucleotide sequences of SEQ ID NOs: 1 or 2. Such genes may be isolated by hybridizing the rat or human sequence (immobilized on a membrane) with a cDNA or genomic library from another mammal under stringent hybridization conditions, for example, at 37° C. in a solution containing 6×SSC, 1×Denhart's solution, 20 ug/ml yeast tRNA (Sigma), and 0.05% sodium pyrophosphate, according to methods that are well known. Thus, the present invention also encompasses related sequences in other mammalian species which can be isolated without undue experimentation.

To facilitate the detection of the desired coding sequence, the a DNA probe may be employed which is labeled with a detectable group. This group can be any material having a detectable physical or chemical property. Such materials are well-known in the field of nucleic acid hybridization and any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113:237 (1977) or by T4 DNA polymerase replacement synthesis as described in, for example, Deen, K. C., et al., *Anal. Biochem.* 135:456 (1983).

Alternatively, oligonucleotide probes may be labeled with a non-radioactive marker such as biotin, an enzyme or a fluorescent group. See, for example, Leary, J. J., et al., *Proc. Natl. Acad. Sci. USA* 80:4045 (1983); Renz, M., et al., *Nucl. Acids Res.* 12:3435 (1984); and Renz, M., *EMBO J.* 6:817 (1983).

To express any of the genes herein, transcriptional and translational signals recognizable by an appropriate host are necessary. The cloned coding sequences, obtained through the methods described herein, may be operably linked to sequences controlling transcriptional expression in an expression vector and introduced into a host cell, either prokaryote or eukaryote, to produce recombinant protein or a functional derivative thereof. Depending upon which strand of the sequence is operably linked to the sequences controlling transcriptional expression, it is also possible to express antisense RNA or a functional derivative thereof.

Expression of the protein in different hosts may result in different post-translational modifications which may alter the properties of the protein. Preferably, the present invention encompasses the expression of bcl-y or a functional derivative thereof, in eukaryotic cells, and especially mammalian, insect and yeast cells. Especially preferred eukaryotic hosts are mammalian cells either in vivo, or in tissue culture. Mammalian cells provide post-translational modifications which should be similar or identical to those found in the native protein. Preferred mammalian host cells include rat-1 fibroblasts, mouse bone marrow derived mast cells, mouse mast cells immortalized with Kirsten sarcoma virus, or normal mouse mast cells that have been co-cultured with mouse fibroblasts. Razin et al., *J. of Immun.* 132:1479 (1984); Levi-Schaffer et al., *Proc. Natl. Acad. Sci.* (USA) 83:6485 (1986) and Reynolds et al., "Immortalization of Murine Connective Tissue-type Mast Cells at Multiple Stages of Their Differentiation by Coculture of Splenocytes with Fibroblasts that Produce Kirsten Sarcoma Virus," *J. Biol. Chem.* 263:12783–12791 (1988).

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide. An operable linkage is a linkage in which a coding sequence is connected to a regulatory sequence (or sequences) in such a way as to place expression of the coding sequence under the influence or control of the regulatory sequence. Two DNA sequences (e.g. the coding sequence of protein and a promoter) are said to be operably linked if induction of promoter function results in the transcription of the coding sequence and if the nature of the linkage between the two DNA sequences does not (1) result in the introduction of a frame-shift mutation; (2) interfere with the ability of regulatory sequences to direct the expression of the coding sequence, antisense RNA, or protein; or (3) interfere with the ability of the coding sequence template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene.

Expression of proteins of the invention in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, Simian virus, herpes virus, or the like. Preferably, these regulatory signals are associated with a particular gene which is capable of a high level of expression in the host cell.

In eukaryotes, where transcription is not linked to translation, control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); in yeast, the yeast gal4 gene promoter (Johnston, S. A., et al., *Proc. Natl. Acad. Sci.* (*USA*) 79:6971–6975 (1982); Silver, P. A., et al., *Proc. Natl. Acad. Sci.* (*USA*) 81:5951–5955 (1984)) or a glycolytic gene promoter may be used.

It is known that translation of eukaryotic mRNA is initiated at the codon which encodes the first methionine. For this reason, it is preferable to ensure that the linkage between a eukaryotic promoter and a DNA sequence which encodes the proteins of the invention or functional derivatives thereof, does not contain any intervening codons which are capable of encoding a methionine. The presence of such codons results either in the formation of a fusion protein or a frame-shift mutation.

It is also possible to stimulate expression of the bcl-y gene in mammalian cells in vitro, in vivo and ex vivo by inserting a DNA regulatory element which is capable of promoting the expression of the native bcl-y gene in that cell, the regulatory element being inserted to as to be operatively linked to the native bcl-y gene. The insertion is accomplished by homologous recombination by creating a DNA construct including a segment of the 5'-terminus of the bcl-y gene and the DNA regulatory element to induce gene transcription. Methods for preparing DNA constructs useful for homologous recombination and methods for transforming mammalian cells are described in U.S. Pat. No. 5,272,071 as well in WO 90/11354, WO 95/31560 (U.S. application Ser. No. 08/243,391), and WO 91/06667 (U.S. application Ser. No. 07/432,069). Thus, the invention also relates to a DNA construct comprising the gene coding for bcl-y in operable linkage to a heterologous regulatory element, e.g. a promoter. In general, such a promoter is a strong promoter in mammalian cells. Such a promoter may be an inducible promoter that is induced only in the presence of an inducing agent. Such a promoter allows for the expression of bcl-y to be turned on and off in the mammalian cells.

When the mammalian cells is a neuronal cell, a neuronal specific promoter may be used. Such promoters are described, for example, by Byrne and Ruddle, *Proc. Natl. Acad. Sci USA* 86:5473–5477 (1989); Gordon, J. et al., *Cell* 50:445–452 (1987); Gloster et al., *J Neurosci.* 14:7319–7330 (1994); Sasahara et al., *Cell* 64:217–227 (1991)); McConlogue et al., *Aging* 15:S12 (1994); Higgins et al., *Ann Neurol.* 35:598–607 (1995); Mucke et al., *Brain Res.* 666:151–167 (1994); Higgins et al., *Proc. Natl. Acad Sci USA* 92:4402–4406 (1995); U.S. Pat. Nos. 5,569,827, U.S. Pat. No. 5,387,742, and 5,082,670; U.S. application Ser. Nos. 08/358,627, 08/096,944, 08/215,083, 07/817,584, 07/915,469 08/486,018, 08/486,538 and 08/480,653; WO95/03397; WO091/02788; WO095/25795; WO93/14200; WO96/40895; WO096/40896; and EP 0 171 105.

If desired, a fusion product of the proteins may be constructed. For example, the sequence coding for the proteins may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of operably linked genes can be modulated. Of interest are regulatory signals which are temperature-sensitive so that by varying the temperature, expression can be repressed or initiated, or are subject to chemical regulation, e.g., metabolite.

If desired, the non-transcribed and/or non-translated regions 3' to the sequence coding for the proteins can be obtained by the above-described cloning methods. The 3'-non-transcribed region may be retained for transcriptional termination regulatory sequence elements; the 3'-non-translated region may be retained for translational termination regulatory sequence elements, or for those elements which direct polyadenylation in eukaryotic cells. Where native expression control signals do not function satisfactorily in a host cell, functional sequences may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the DNA construct into the host cell chromosomal DNA, or to allow it to exist in extrachromosomal form. If the protein encoding sequence and an operably linked promoter are introduced into a recipient eukaryotic cell as a non-replicating DNA (or RNA) molecule, the expression of the protein may occur through the transient expression of the introduced sequence.

In a preferred embodiment, genetically stable transformants may be constructed with vector systems, or transformation systems, whereby bcl-y DNA is integrated into the host chromosome or where a promoter is inserted in operable linkage to the bcl-y gene in the chromosome. Such integration may occur by homologous recombination, de novo within the cell or, in a most preferred embodiment, through the aid of a cotransformed vector which functionally inserts itself into the host chromosome, for example, retroviral vectors, transposons or other DNA elements which promote integration of DNA sequences in chromosomes. Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection. In another embodiment, the introduced sequence is incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise*, Vol. 3, *Gene Expression*, Academic Press, NY, pp. 563–608 (1980)), and are commercially available.

Once the vector or DNA sequence containing the construct(s) is prepared for expression, the DNA construct(s) is introduced into an appropriate host cell by any of a variety of suitable means, including transfection. After the introduction of the vector, recipient cells are grown in a medium which selects for the growth of vector-containing cells. Expression of the cloned gene sequence(s) results in the production of the protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like). The latter is preferred for the expression of the proteins of the invention. By growing cells under conditions in which the proteins are not expressed, cell death may be avoided. When a high cell density is reached, expression of the proteins may be induced and the recombinant protein harvested immediately before death occurs.

The expressed protein is isolated and purified in accordance with conventional procedures, such as extraction, precipitation, gel filtration chromatography, affinity chromatography, electrophoresis, or the like. Preferably, an affinity column consisting of $Ni^{2+}$ ions immobilized to the chelating adsorbent nitrilo-tri-acetic acid (NTA) is employed.

The present invention also relates to substantially pure bcl-y proteins. Such proteins are considered substantially pure when they are free of other proteins naturally associated therewith. Substantial purity may be evidenced, for example, by one band on SDS-PAGE.

The bcl-y sequences, obtained through the methods above, will provide sequences which not only encode these proteins but which also encode antisense RNA directed against bcl-y DNA; the antisense DNA sequence will be that sequence found on the opposite strand of the strand transcribing the mRNA. The antisense DNA strand may also be operably linked to a promoter in an expression vector such that transformation with this vector results in a host capable of expression of the antisense RNA in the transformed cell. Antisense DNA and RNA may be used to interact with endogenous bcl-y DNA or RNA in a manner which inhibits or represses transcription or translation of the genes in a highly specific manner. Use of antisense nucleic acid to block gene expression is discussed in Lichtenstein, C., *Nature* 333:801–802 (1988).

Methods of Using

The genes coding for mammalian, e.g. rat and human, bcl-y may be used for a number of distinct purposes. First, portions of the gene may be used as a probe for identifying homologous genes in other mammals. Such probes may also be used to determine whether the bcl-y gene or homologs thereof are being expressed in cells.

The genes may also be used in the development of therapeutic methods for diseases and conditions characterized by cell death. Among diseases and conditions which could potentially be treated are neural and muscular degenerative diseases, myocardial infarction, stroke, vitally induced cell death, aging and spinal cord injury. See, *Bioworld Today* 20:1 and 5 (Jan. 30, 1997), which discloses that expression of the related gene bcl-2 in transgenic animals results in the ability of the mice to regenerate nerve cells that have been severed during neurosurgery. In this embodiment, the gene may be inserted into the nerve cells under control of a neuronal specific promoter. Therapeutics based upon bcl-y genes and related cell death genes may also be developed.

The ability to prevent vertebrate programmed cell death is of use in developing cells which can be maintained for an indefinite period of time in culture. The ability to prevent programmed cell death may allow cells to live independent of normally required growth factors. If the bcl-y is involved in inducing cell death, one way of preventing the cell death is by providing to the cells antisense bcl-y RNA according to methods described above.

Alternatively, the expression of genes coding for bcl-y may be increased in order to cause programmed cell death. For example, homologous recombination may be used to replace a defective region of a gene coding for bcl-y with its normal counterpart. In this way, it may be possible to prevent the uncontrolled growth of certain malignant cells, in particular, Kaposi's sarcoma, and lung cancer. Methods of increasing bcl-y expression may be used to kill undesired organisms such as parasites. In this embodiment, the gene coding for bcl-y is transfected into the cell as part of a vector which contains control elements recognized by the host.

Methods for transfecting DNA into host cells, in particular, mammalian cells for gene therapy are taught for example in U.S. Pat. No. 5,399,346 to Anderson et al., Cotten et al., *Proc. Natl. Acad. Sci USA* 87:4033–4037 (1990), Cotten et al., *Proc. Natl. Acad. Sci USA* 89:6094–6098 (1992), Curiel et al., *Proc. Natl. Acad. Sci USA* 88:8850–8854 (1991), Curiel et al., *Am. J. Resp. Cell Mol. Biol* 6:247–252 (1992), Curiel et al., *J. Cell. Biochem. Suppl.* 60:Q407 (1992), Wagner et al., *Proc. Natl. Acad. Sci USA* 87:3410–3414 (1990), Wagner et al., *Proc. Natl. Acad. Sci USA* 88:4255–4259 (1991), and Wagner et al., *Bioconjugate Chem.* 2:226–231 (1991).

If the genes instead are involved in preventing nerve cell death, the genes of the present invention may be transfected into cells in order to immortalize them. Such immortalized cells are useful for cell culture to produce recombinant proteins. Further, antisense RNA that is capable of hybridizing bcl-y DNA may be used to inhibit the expression of bcl-y in malignant cells, leading to apoptosis.

An IND for multiple sclerosis has been approved for Anergen, Inc. to develop their MS-AnergiA that causes autoantigenic T cell apoptosis. Thus, a further use of the expression product of the bcl-y gene is in the treatment of multiple sclerosis.

Having now generally described this invention, the same will be further described by reference to certain specific examples which are provided herein for purposes of illustration only and are not intended to be limiting unless otherwise specified. All references cited throughout the specification are incorporated by reference in their entirety.

EXAMPLE

Methods
Source of PCR Templates mRNA was isolated from rat brain and other tissues with conventional methods and converted into single-stranded cDNA for use as a PCR template. Rat genomic DNA was isolated from spleen by conventional methods or obtained from commercial sources.

PCR Primer Design and Cycling Parameters

The upstream and downstream PCR primers had the sequences:

AT(T/C) TGG GGN (A/C)GN AT(T/C/A) GTN GC (primer-bcl-u) (SEQ ID NO:7) and CCA NCC NCC (A/G)TT (A/G)TC (T/C/)TG (A/G/T)AT CCA (primer-bcl-d) (SEQ ID NO:8). These sequences encode the peptides NWGRIVA (SEQ ID NO:9) and WIQDNGGW (SEQ ID NO: 10), respectively. Polymerase chain reactions were performed using the following cycling parameters: (1) Denaturation step: 94° C. for 1 minute; (2) Annealing step: 45° C., 50° C., or 55° C. for 4 minutes; (3) Extension step: 72° C. for 2 minutes. The number of cycles ranged from 25 to 35 depending on the experiment.

Cloning and Sequencing

PCR products of the appropriate size were cloned into a TA-cloning vector and sequenced using an Applied Biosystems automated DNA sequencer. In order to obtain full-length clones, the cloned PCR products were gel-purified, labeled with $^{32}$P-CTP, and used as hybridization probes to screen commercially-available rat and human cDNA libraries.

Expression Vectors

Both the rat and human bcl-y cDNAs were subcloned into the mammalian cell expression vectors pCI and pRc/CMV (Table 3). These expression constructs will be used for both transient and stable expression of the bcl-y genes and will allow a determination of the cellular function of this gene (i.e., whether it is a cell death blocker or cell death promoter).

Protein Expression

The human bcl-y cDNA was tagged at the 3' end of the open reading frame with a nucleotide sequence encoding six consecutive histidine residues and subcloned into the bacterial expression vector pQE60. This expression construct was transfected into the bacterial strain M15[pREP4] and bcl-y expression was induced by the addition of IPTG. Bcl-y protein was purified from crude bacterial extracts using an affinity column consisting of $Ni^{2+}$ ions immobilized to the chelating adsorbent nitrilo-tri-acetic acid (NTA). The degree of purification was monitored by SDS-PAGE.

Analysis of Tissue Expression

Northern blots were prepared using conventional techniques.

Results

Identification of Bcl-y, a Novel Bcl-2 Homologue

In order to find new members of the bcl-2 family, two degenerate oligonucleotides (bcl-u and bcl-d) were prepared and used as upstream and downstream primers in a PCR reaction. The sequences used to design these primers were portions of the bcl-2 homology domains 1 and 2, as defined by multiple alignments between bcl-2 and two of its previously identified homologues, bcl-x and BAX. Two different types of template were used: rat brain cDNA and rat genomic DNA. When primary bcl-u and bcl-d were applied to these templates in the PCR, products of the expected length were observed on agarose gels, and the DNA fragments on these gels were cloned and sequenced. Analysis of these sequences revealed four classes of fragments. Three classes of PCR products represented fragments of bcl-2, bcl-x and BAX. One class represented a novel but related sequence and it was designated bcl-y.

The bcl-y PCR product was used to screen a rat brainstem cDNA library in order to obtain a full-length clone. Five cDNA clones were isolated and sequenced. One of these (clone 3a) contained a full-length open reading frame (ORF) and was used to screen a human brain cDNA library. Of five human brain cDNAs isolated, one (clone 14) was full-length in the ORF and was used for further analysis and manipulations.

Sequence Analysis of Rat and Human Bcl-y

Analysis of the rat and human bcl-y cDNAs (SEQ ID NOs: 1 and 2) reveals an ORF of 579 bp coding for a protein of 193 amino acids with a molecular weight of about 20,832 kDa. The rat and human proteins are highly homologous, showing 96% sequence identity. Both the rat and human bcl-y genes (SEQ ID NOs: 1 and 2) and protein products (SEQ ID NOs: 3 and 4) are closely related to the other known members of the bcl-2 family (FIGS. 1 and 2 and Table 2). The closest relative to bcl-y is bcl-x, with which it shows about a 59% homology at the amino acid level. Regions of homology can be found throughout the length of the protein, but are particularly pronounced in regions that are highly conserved in all members of the bcl-2 family (regions BH1 and BH2, see FIGS. 3B and 3C). In addition, bcl-y contains at its C-terminus a region homologous to a signal sequence known to regulate the insertion of proteins into intracellular membranes (FIG. 3D). Based on these sequence comparisons, it is predicted that bcl-y possesses some of the same properties of the other members of the bcl-2 family, i.e., it will be localized at mitochondria and other internal membranes and will function to either block or promote cell death.

Tissue Distribution of Bcl-y mRNA

To determine which tissue expresses bcl-y, Northern blots (RNA blots) are prepared containing mRNA from various rat tissues and from human tumor cell lines. Preliminary results suggest that the rat bcl-y gene produces a single transcript about 2.4 kb long. In an autoradiograph containing both brain and liver mRNA, the signal from brain was about 5-fold higher than the signal from liver suggesting that bcl-y may be enriched in the nervous system. However, a definitive answer to this question will require analysis of a wider range of organs.

Production of Recombinant Human Bcl-y Protein

In order to manufacture antibodies to the human bcl-y protein, we are producing high levels of the recombinant bcl-y protein using the 6XHis/Nickel Affinity Column system. In this method, the human bcl-y cDNA is subcloned into the bacterial high-level expression vector pQE60 together with a nucleotide sequence that attaches a tag consisting of six histidine residues in the protein product. The affinity of these multiple histidines for the nickel-containing resin allows an easy and efficient purification away from other proteins. Thus far, we have shown that our expression constructs produce ample protein product of the appropriate size at a purity of about 80% of the total cellular proteins. However, since such protein is free of the proteins which naturally contaminate it, it is "substantially pure."

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

TABLE 1

Bcl-2 Family Members

| Gene | Effect | Tissue Distribution |
| --- | --- | --- |
| bcl-2 | Survival | Many tissues, incl. n.s.[1] |
| bcl-x | Survival | Many tissues, esp. n.s. |
| BAX | Death | Many tissues, incl. n.s. |
| MCL-1 | ? | Not reported |
| A1 | ? | Not reported |
| LMW5-HL | ? | Viral (ASFV) |
| BHRF1 | ? | Viral (EBV) |
| Q01001 | ? | Viral (HSV) |
| ced-9 | Survival | Nematode |
| BAD | Death | Immune cells, other tissues? |
| BAK | Death | Many tissues, incl. n.s. |
| NR-13 | ? | Neural, muscular tissues |

[1] n.s. = nervous system.

TABLE 2

Percent Homologies between Bcl-y and its Closest Relatives

|  | bcl-x | bcl-2 | BAX | MCL1 |
| --- | --- | --- | --- | --- |
| bcl-y | 46/13 | 43/17 | 19/20 | 16/17 |
| MCL1 | 13/6 | 18/7 | 23/10 | — |
| BAX | 17/6 | 20/10 | — | — |
| bcl-2 | 43/12 | — | — | — |

TABLE 3

Bcl-y Expression Constructs

| Construct | Intended Use |
| --- | --- |
| pCI/hbcl-y | Transient and Stable Cell Lines |
| pRc/CMV/hbcl-y | Transient and Stable Cell Lines |
| pQE60/hbcl-y | Protein Expression |

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 579 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:1:

```
ATGGCGACCC CAGCCTCAAC CCCAGACACA CGGGCTCTAG TGGCTGACTT TGTAGGCTAT        60

AAGCTGAGAC AGAAGGGTTA TGTCTGTGGA GCTGGCCCTG GGGAAGGCCC AGCAGCCGAC       120

CCGCTGCACC AAGCCATGCG GGCAGCTGGA GACGAGTTTG AGACCCGCTT CCGGCGCACC       180
```

```
TTCTCTGACC  TGGCCGCTCA  GCTACACGTG  ACCCCAGGCT  CAGCCCAGCA  ACGCTTCACC    240
CAGGTTTCCG  ACGAACTTTT  CCAAGGGGGC  CCCAACTGGG  GCCGTCTTGT  GGCATTCTTT    300
GTCTTTGGGG  CTGCCCTGTG  TGCTGAGAGT  GTCAACAAAG  AAATGGAGCC  ATTGGTGGGA    360
CAAGTGCAGG  ATTGGATGGT  GACCTACCTG  GAGACACGCT  TGGCTGACTG  GATCCACAGC    420
AGTGGGGGCT  GGGCGGAGTT  CACAGCTCTA  TACGGGGACG  GGGCCCTGGA  GGAGGCACGG    480
CGTCTGCGGG  AGGGGAACTG  GGCATCAGTG  AGGACAGTGC  TGACGGGGC   TGTGGCACTG    540
GGGGCCCTGG  TAACTGTAGG  GGCCTTTTTT  GCTAGCAAG                             579
```

( 2 ) INFORMATION FOR SEQ ID NO:2:

( i ) SEQUENCE CHARACTERISTICS:
        ( A ) LENGTH: 579 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:2:

```
ATGGCGACCC  CAGCCTCGGC  CCCAGACACA  CGGGCTCTGG  TGGAAGACTT  TGTAGGTTAT    60
AAGCTGAGGC  AGAAGGGTTA  TGTCTGTGGA  GCTGGCCCCG  GGAGGGCCC   AGCAGCTGAC   120
CCACTGCACC  AAGCCATGCG  GGCAGCTGGA  GATGAGTTCG  AGACCCGCTT  CCGGCGCACC   180
TTCTCTGATC  TGGCGGCTCA  GCTGCATGTG  ACCCCAGGCT  CAGCCCAACA  ACGCTTCACC   240
CAGGTCTCCG  ATGAACTTTT  TCAAGGGGGC  CCCAACTGGG  GCCGCCTTGT  AGCCTTCTTT   300
GTCTTTGGGG  CTGCACTGTG  TGCTGAGAGT  GTCAACAAGG  AGATGGAACC  ACTGGTGGGA   360
CAAGTGCAGG  AGTGGATGGT  GGCCTACCTG  GAGACGCGGC  TGGCTGACTG  GATCCACAGC   420
AGTGGGGGCT  GGGCGGAGTT  CACAGCTCTA  TACGGGACG   GGGCCCTGGA  GGAGCGCGG    480
CGTCTGCGGG  AGGGGAACTG  GGCATCAGTG  AGGACAGTGC  TGACGGGGC   CGTGGCACTG   540
GGGGCCCTGG  TAACTGTAGG  GGCCTTTTTT  GCTAGCAAG                            579
```

( 2 ) INFORMATION FOR SEQ ID NO:3:

( i ) SEQUENCE CHARACTERISTICS:
        ( A ) LENGTH: 193 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

```
Met  Ala  Thr  Pro  Ala  Ser  Thr  Pro  Asp  Thr  Arg  Ala  Leu  Val  Ala  Asp
  1              5                        10                       15

Phe  Val  Gly  Tyr  Lys  Leu  Arg  Gln  Lys  Gly  Tyr  Val  Cys  Gly  Ala  Gly
                20                       25                       30

Pro  Gly  Glu  Gly  Pro  Ala  Ala  Asp  Pro  Leu  His  Gln  Ala  Met  Arg  Ala
            35                       40                       45

Ala  Gly  Asp  Glu  Phe  Glu  Thr  Arg  Phe  Arg  Arg  Thr  Phe  Ser  Asp  Leu
       50                       55                       60

Ala  Ala  Gln  Leu  His  Val  Thr  Pro  Gly  Ser  Ala  Gln  Gln  Arg  Phe  Thr
 65                       70                       75                       80

Gln  Val  Ser  Asp  Glu  Leu  Phe  Gln  Gly  Gly  Pro  Asn  Trp  Gly  Arg  Leu
                     85                       90                       95

Val  Ala  Phe  Phe  Val  Phe  Gly  Ala  Ala  Leu  Cys  Ala  Glu  Ser  Val  Asn
               100                      105                      110
```

```
Lys Glu Met Glu Pro Leu Val Gly Gln Val Gln Asp Trp Met Val Thr
        115             120                 125

Tyr Leu Glu Thr Arg Leu Ala Asp Trp Ile His Ser Ser Gly Gly Trp
    130             135                 140

Ala Glu Phe Thr Ala Leu Tyr Gly Asp Gly Ala Leu Glu Glu Ala Arg
145                 150             155                     160

Arg Leu Arg Glu Gly Asn Trp Ala Ser Val Arg Thr Val Leu Thr Gly
            165             170                 175

Ala Val Ala Leu Gly Ala Leu Val Thr Val Gly Ala Phe Phe Ala Ser
            180             185                 190

Lys
```

(2) INFORMATION FOR SEQ ID NO:4:

(i) SEQUENCE CHARACTERISTICS:
    (A) LENGTH: 193 amino acids
    (B) TYPE: amino acid
    (C) STRANDEDNESS: Not Relevant
    (D) TOPOLOGY: linear (ii) MOLECULE TYPE: protein (xi) SEQUENCE DESCRIPTION: SEQ ID NO:4:

```
Met Ala Thr Pro Ala Ser Ala Pro Asp Thr Arg Ala Leu Val Glu Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys
```

(2) INFORMATION FOR SEQ ID NO:5:

(i) SEQUENCE CHARACTERISTICS:
    (A) LENGTH: 192 amino acids
    (B) TYPE: amino acid
    (C) STRANDEDNESS: Not Relevant
    (D) TOPOLOGY: linear (ii) MOLECULE TYPE: protein ( x i ) SEQUENCE DESCRIPTION: SEQ ID NO:5:

| Ala | Thr | Pro | Ala | Ser | Thr | Pro | Asp | Thr | Arg | Ala | Leu | Val | Ala | Asp | Phe |
|---|---|---|---|---|---|---|---|---|---|---|---|---|---|---|---|
| 1 | | | | 5 | | | | | 10 | | | | | 15 | |

| Val | Gly | Tyr | Lys | Leu | Arg | Gln | Lys | Gly | Tyr | Val | Cys | Gly | Ala | Gly | Pro |
|---|---|---|---|---|---|---|---|---|---|---|---|---|---|---|---|
| | | | 20 | | | | | 25 | | | | | 30 | | |

| Gly | Glu | Gly | Pro | Ala | Ala | Asp | Pro | Leu | His | Gln | Ala | Met | Arg | Ala | Ala |
|---|---|---|---|---|---|---|---|---|---|---|---|---|---|---|---|
| | | 35 | | | | | 40 | | | | | 45 | | | |

| Gly | Asp | Glu | Phe | Glu | Thr | Arg | Phe | Arg | Arg | Thr | Phe | Ser | Asp | Leu | Ala |
|---|---|---|---|---|---|---|---|---|---|---|---|---|---|---|---|
| | 50 | | | | | 55 | | | | | 60 | | | | |

| Ala | Gln | Leu | His | Val | Thr | Pro | Gly | Ser | Ala | Gln | Gln | Arg | Phe | Thr | Gln |
|---|---|---|---|---|---|---|---|---|---|---|---|---|---|---|---|
| 65 | | | | | 70 | | | | | 75 | | | | | 80 |

| Val | Ser | Asp | Glu | Leu | Phe | Gln | Gly | Gly | Pro | Asn | Trp | Gly | Arg | Leu | Val |
|---|---|---|---|---|---|---|---|---|---|---|---|---|---|---|---|
| | | | | 85 | | | | | 90 | | | | | 95 | |

| Ala | Phe | Phe | Val | Phe | Gly | Ala | Ala | Leu | Cys | Ala | Glu | Ser | Val | Asn | Lys |
|---|---|---|---|---|---|---|---|---|---|---|---|---|---|---|---|
| | | | 100 | | | | | 105 | | | | | 110 | | |

| Glu | Met | Glu | Pro | Leu | Val | Gly | Gln | Val | Gln | Asp | Trp | Met | Val | Thr | Tyr |
|---|---|---|---|---|---|---|---|---|---|---|---|---|---|---|---|
| | | 115 | | | | | 120 | | | | | 125 | | | |

| Leu | Glu | Thr | Arg | Leu | Ala | Asp | Trp | Ile | His | Ser | Ser | Gly | Gly | Trp | Ala |
|---|---|---|---|---|---|---|---|---|---|---|---|---|---|---|---|
| | 130 | | | | | 135 | | | | | 140 | | | | |

| Glu | Phe | Thr | Ala | Leu | Tyr | Gly | Asp | Gly | Ala | Leu | Glu | Glu | Ala | Arg | Arg |
|---|---|---|---|---|---|---|---|---|---|---|---|---|---|---|---|
| 145 | | | | | 150 | | | | | 155 | | | | | 160 |

| Leu | Arg | Glu | Gly | Asn | Trp | Ala | Ser | Val | Arg | Thr | Val | Leu | Thr | Gly | Ala |
|---|---|---|---|---|---|---|---|---|---|---|---|---|---|---|---|
| | | | | 165 | | | | | 170 | | | | | 175 | |

| Val | Ala | Leu | Gly | Ala | Leu | Val | Thr | Val | Gly | Ala | Phe | Phe | Ala | Ser | Lys |
|---|---|---|---|---|---|---|---|---|---|---|---|---|---|---|---|
| | | | 180 | | | | | 185 | | | | | 190 | | |

( 2 ) INFORMATION FOR SEQ ID NO:6:

( i ) SEQUENCE CHARACTERISTICS:
        ( A ) LENGTH: 192 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

| Ala | Thr | Pro | Ala | Ser | Ala | Pro | Asp | Thr | Arg | Ala | Leu | Val | Glu | Asp | Phe |
|---|---|---|---|---|---|---|---|---|---|---|---|---|---|---|---|
| 1 | | | | 5 | | | | | 10 | | | | | 15 | |

| Val | Gly | Tyr | Lys | Leu | Arg | Gln | Lys | Gly | Tyr | Val | Cys | Gly | Ala | Gly | Pro |
|---|---|---|---|---|---|---|---|---|---|---|---|---|---|---|---|
| | | | 20 | | | | | 25 | | | | | 30 | | |

| Gly | Glu | Gly | Pro | Ala | Ala | Asp | Pro | Leu | His | Gln | Ala | Met | Arg | Ala | Ala |
|---|---|---|---|---|---|---|---|---|---|---|---|---|---|---|---|
| | | 35 | | | | | 40 | | | | | 45 | | | |

| Gly | Asp | Glu | Phe | Glu | Thr | Arg | Phe | Arg | Arg | Thr | Phe | Ser | Asp | Leu | Ala |
|---|---|---|---|---|---|---|---|---|---|---|---|---|---|---|---|
| | 50 | | | | | 55 | | | | | 60 | | | | |

| Ala | Gln | Leu | His | Val | Thr | Pro | Gly | Ser | Ala | Gln | Gln | Arg | Phe | Thr | Gln |
|---|---|---|---|---|---|---|---|---|---|---|---|---|---|---|---|
| 65 | | | | | 70 | | | | | 75 | | | | | 80 |

| Val | Ser | Asp | Glu | Leu | Phe | Gln | Gly | Gly | Pro | Asn | Trp | Gly | Arg | Leu | Val |
|---|---|---|---|---|---|---|---|---|---|---|---|---|---|---|---|
| | | | | 85 | | | | | 90 | | | | | 95 | |

| Ala | Phe | Phe | Val | Phe | Gly | Ala | Ala | Leu | Cys | Ala | Glu | Ser | Val | Asn | Lys |
|---|---|---|---|---|---|---|---|---|---|---|---|---|---|---|---|
| | | | 100 | | | | | 105 | | | | | 110 | | |

| Glu | Met | Glu | Pro | Leu | Val | Gly | Gln | Val | Gln | Glu | Trp | Met | Val | Ala | Tyr |
|---|---|---|---|---|---|---|---|---|---|---|---|---|---|---|---|
| | | 115 | | | | | 120 | | | | | 125 | | | |

| Leu | Glu | Thr | Arg | Leu | Ala | Asp | Trp | Ile | His | Ser | Ser | Gly | Gly | Trp | Ala |
|---|---|---|---|---|---|---|---|---|---|---|---|---|---|---|---|
| | 130 | | | | | 135 | | | | | 140 | | | | |

| Glu | Phe | Thr | Ala | Leu | Tyr | Gly | Asp | Gly | Ala | Leu | Glu | Glu | Ala | Arg | Arg |
|---|---|---|---|---|---|---|---|---|---|---|---|---|---|---|---|
| 145 | | | | | 150 | | | | | 155 | | | | | 160 |

```
        Leu  Arg  Glu  Gly  Asn  Trp  Ala  Ser  Val  Arg  Thr  Val  Leu  Thr  Gly  Ala
                            165                      170                      175

Val  Ala  Leu  Gly  Ala  Leu  Val  Thr  Val  Gly  Ala  Phe  Phe  Ala  Ser  Lys
                            180                      185                      190
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:7:

ATYTGGGGNM GNATHGTNGC                                                                          20

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:8:

CCANCCNCCR TTRTCYTGDA TCCA                                                                     24

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:9:

```
        Asn  Trp  Gly  Arg  Ile  Val  Ala
        1                   5
```

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:10:

```
        Trp  Ile  Gln  Asp  Asn  Gly  Gly  Trp
        1                   5
```

(2) INFORMATION FOR SEQ ID NO:11:

(i) SEQUENCE CHARACTERISTICS:
        (A) LENGTH: 142 amino acids
        (B) TYPE: amino acid
        (C) STRANDEDNESS: Not Relevant
        (D) TOPOLOGY: linear (ii) MOLECULE TYPE: peptide ( x i ) SEQUENCE DESCRIPTION: SEQ ID NO:11:

| Met | Ala | His | Ala | Gly | Arg | Thr | Gly | Tyr | Asp | Asn | Arg | Glu | Ile | Val | Met |
| 1 | | | | 5 | | | | | 10 | | | | | | 15 |
| Lys | Tyr | Ile | His | Tyr | Lys | Leu | Ser | Gln | Arg | Gly | Tyr | Glu | Trp | Asp | Ala |
| | | | 20 | | | | | 25 | | | | | 30 | | |
| Gly | Asp | Val | Gly | Ala | Ala | Pro | Pro | Gly | Ala | Ala | Pro | Ala | Pro | Gly | Ile |
| | | | 35 | | | | 40 | | | | | 45 | | | |
| Phe | Ser | Ser | Gln | Pro | Gly | His | Thr | Pro | His | Pro | Ala | Ala | Ser | Arg | Asp |
| | 50 | | | | | 55 | | | | | 60 | | | | |
| Pro | Val | Ala | Arg | Thr | Ser | Pro | Leu | Gln | Thr | Pro | Ala | Ala | Pro | Gly | Ala |
| 65 | | | | | 70 | | | | | 75 | | | | | 80 |
| Ala | Ala | Gly | Pro | Ala | Leu | Ser | Pro | Val | Pro | Pro | Val | Val | His | Leu | Ala |
| | | | | 85 | | | | | 90 | | | | | 95 | |
| Leu | Arg | Gln | Ala | Gly | Asp | Asp | Phe | Ser | Arg | Arg | Tyr | Arg | Gly | Asp | Phe |
| | | | | 100 | | | | | 105 | | | | | 110 | |
| Ala | Glu | Met | Ser | Ser | Gln | Leu | His | Leu | Thr | Pro | Phe | Thr | Ala | Arg | Gly |
| | | | 115 | | | | | 120 | | | | | 125 | | |
| Arg | Phe | Ala | Thr | Val | Val | Glu | Glu | Leu | Phe | Arg | Asp | Gly | Val |
| | | | 130 | | | | 135 | | | | 140 | | |

( 2 ) INFORMATION FOR SEQ ID NO:12:

( i ) SEQUENCE CHARACTERISTICS:
       ( A ) LENGTH: 62 amino acids
       ( B ) TYPE: amino acid
       ( C ) STRANDEDNESS: Not Relevant
       ( D ) TOPOLOGY: linear ( i i ) MOLECULE TYPE: peptide ( x i ) SEQUENCE DESCRIPTION: SEQ ID NO:12:

| Asn | Trp | Gly | Arg | Ile | Val | Ala | Phe | Phe | Glu | Phe | Gly | Gly | Val | Met | Cys |
| 1 | | | | 5 | | | | | 10 | | | | | 15 | |
| Val | Glu | Ser | Val | Asn | Arg | Glu | Met | Ser | Pro | Leu | Val | Asp | Asn | Ile | Ala |
| | | | 20 | | | | | 25 | | | | | 30 | | |
| Leu | Trp | Met | Thr | Glu | Tyr | Leu | Asn | Arg | His | Leu | His | Thr | Trp | Ile | Gln |
| | | | 35 | | | | | 40 | | | | | 45 | | |
| Asp | Asn | Gly | Gly | Trp | Asp | Ala | Phe | Val | Glu | Leu | Tyr | Gly | Pro |
| | 50 | | | | | 55 | | | | | 60 | | |

( 2 ) INFORMATION FOR SEQ ID NO:13:

( i ) SEQUENCE CHARACTERISTICS:
       ( A ) LENGTH: 21 amino acids
       ( B ) TYPE: amino acid
       ( C ) STRANDEDNESS: Not Relevant
       ( D ) TOPOLOGY: linear ( i i ) MOLECULE TYPE: peptide ( x i ) SEQUENCE DESCRIPTION: SEQ ID NO:13:

| Ser | Met | Arg | Pro | Leu | Phe | Asp | Phe | Ser | Trp | Leu | Ser | Leu | Lys | Thr | Leu |
| 1 | | | | 5 | | | | | 10 | | | | | 15 | |
| Leu | Ser | Leu | Ala | Leu |
| | | | 20 | |

( 2 ) INFORMATION FOR SEQ ID NO:14:

( i ) SEQUENCE CHARACTERISTICS:
       ( A ) LENGTH: 14 amino acids
       ( B ) TYPE: amino acid
       ( C ) STRANDEDNESS: Not Relevant ( D ) TOPOLOGY: linear ( i i ) MOLECULE TYPE: peptide ( x i ) SEQUENCE DESCRIPTION: SEQ ID NO:14:

```
Val Gly Ala Cys Ile Thr Leu Gly Ala Tyr Leu Ser His Lys
1               5                   10
```

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:15:

```
Met Ser Gln Ser
1
```

( 2 ) INFORMATION FOR SEQ ID NO:16:

( i ) SEQUENCE CHARACTERISTICS:
        ( A ) LENGTH: 84 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:16:

```
Asn Arg Glu Leu Val Val Asp Phe Leu Ser Tyr Lys Leu Ser Gln Lys
1               5                   10                  15

Gly Tyr Ser Trp Ser Gln Phe Ser Asp Val Glu Glu Asn Arg Thr Glu
                20                  25                  30

Ala Pro Glu Gly Thr Glu Ser Glu Met Glu Thr Pro Ser Ala Ile Asn
            35                  40                  45

Gly Asn Pro Ser Trp His Leu Ala Asp Ser Pro Ala Val Asn Gly Ala
        50                  55                  60

Thr Gly His Ser Ser Ser Leu Asp Ala Arg Glu Val Ile Pro Met Ala
65                  70                  75                  80

Ala Val Lys Gln
```

( 2 ) INFORMATION FOR SEQ ID NO:17:

( i ) SEQUENCE CHARACTERISTICS:
        ( A ) LENGTH: 47 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:17:

```
Ala Leu Arg Glu Ala Gly Asp Glu Phe Glu Leu Arg Tyr Arg Arg Ala
1               5                   10                  15

Phe Ser Asp Leu Thr Ser Gln Leu His Ile Thr Pro Gly Thr Ala Tyr
                20                  25                  30

Gln Ser Phe Glu Gln Val Val Asn Glu Leu Phe Arg Asp Gly Val
            35                  40                  45
```

( 2 ) INFORMATION FOR SEQ ID NO:18:

( i ) SEQUENCE CHARACTERISTICS:
  ( A ) LENGTH: 83 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:18:

```
Asn Trp Gly Arg Ile Val Ala Phe Phe Ser Phe Gly Gly Ala Leu Cys
 1               5                  10                   15

Val Glu Ser Val Asp Lys Glu Met Gln Val Leu Val Ser Arg Ile Ala
              20                  25                  30

Ala Trp Met Ala Thr Tyr Leu Asn Asp His Leu Glu Pro Trp Ile Gln
          35                  40                  45

Glu Asn Gly Gly Trp Asp Thr Phe Val Glu Leu Tyr Gly Asn Asn Ala
      50                  55                  60

Ala Ala Glu Ser Arg Lys Gly Gln Glu Arg Phe Asn Arg Trp Phe Leu
 65                  70                  75                  80

Thr Gly Met
```

( 2 ) INFORMATION FOR SEQ ID NO:19:

( i ) SEQUENCE CHARACTERISTICS:
    ( A ) LENGTH: 14 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:19:

```
Val Ala Gly Val Val Leu Leu Gly Ser Leu Phe Ser Arg Lys
 1               5                  10
```

( 2 ) INFORMATION FOR SEQ ID NO:20:

( i ) SEQUENCE CHARACTERISTICS:
    ( A ) LENGTH: 5 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:20:

```
Met Asp Gly Ser Gly
 1               5
```

( 2 ) INFORMATION FOR SEQ ID NO:21:

( i ) SEQUENCE CHARACTERISTICS:
    ( A ) LENGTH: 25 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:21:

```
Glu Gln Pro Arg Gly Gly Gly Pro Thr Ser Ser Glu Gln Ile Met Lys
 1               5                  10                  15

Thr Gly Ala Leu Leu Leu Gln Gly Phe
              20                  25
```

( 2 ) INFORMATION FOR SEQ ID NO:22:

( i ) SEQUENCE CHARACTERISTICS:
  ( A ) LENGTH: 42 amino acids
  ( B ) TYPE: amino acid
  ( C ) STRANDEDNESS: Not Relevant
  ( D ) TOPOLOGY: linear ( i i ) MOLECULE TYPE: peptide ( x i ) SEQUENCE DESCRIPTION: SEQ ID NO:22:

| Ile | Gln | Asp | Arg | Ala | Gly | Arg | Met | Gly | Gly | Glu | Ala | Pro | Glu | Leu | Ala |
|---|---|---|---|---|---|---|---|---|---|---|---|---|---|---|---|
| 1 | | | | 5 | | | | | 10 | | | | | 15 | |
| Leu | Asp | Pro | Val | Pro | Gln | Asp | Ala | Ser | Thr | Lys | Lys | Leu | Ser | Glu | Cys |
| | | | 20 | | | | | 25 | | | | | 30 | | |
| Leu | Lys | Arg | Ile | Gly | Asp | Glu | Leu | Asp | Ser | | | | | | |
| | | 35 | | | | | 40 | | | | | | | | |

( 2 ) INFORMATION FOR SEQ ID NO:23:

( i ) SEQUENCE CHARACTERISTICS:
    ( A ) LENGTH: 10 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:23:

| Asn | Met | Glu | Leu | Gln | Arg | Met | Ile | Ala | Ala |
|---|---|---|---|---|---|---|---|---|---|
| 1 | | | | 5 | | | | | 10 |

( 2 ) INFORMATION FOR SEQ ID NO:24:

( i ) SEQUENCE CHARACTERISTICS:
    ( A ) LENGTH: 87 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:24:

| Val | Asp | Thr | Asp | Ser | Pro | Arg | Glu | Val | Phe | Phe | Arg | Val | Ala | Ala | Asp |
|---|---|---|---|---|---|---|---|---|---|---|---|---|---|---|---|
| 1 | | | | 5 | | | | | 10 | | | | | 15 | |
| Met | Phe | Ser | Asp | Gly | Asn | Phe | Asn | Trp | Gly | Arg | Val | Val | Ala | Leu | Phe |
| | | | 20 | | | | | 25 | | | | | 30 | | |
| Tyr | Phe | Ala | Ser | Lys | Leu | Val | Leu | Lys | Ala | Leu | Cys | Thr | Lys | Val | Pro |
| | | | 35 | | | | | 40 | | | | | 45 | | |
| Glu | Leu | Ile | Arg | Thr | Ile | Met | Gly | Trp | Thr | Leu | Asp | Phe | Leu | Arg | Glu |
| | | 50 | | | | | 55 | | | | | 60 | | | |
| Arg | Leu | Leu | Gly | Trp | Ile | Gln | Asp | Gln | Gly | Gly | Trp | Asp | Gly | Leu | Leu |
| 65 | | | | | 70 | | | | | 75 | | | | | 80 |
| Ser | Tyr | Phe | Gly | Thr | Pro | Thr | | | | | | | | | |
| | | | | 85 | | | | | | | | | | | |

( 2 ) INFORMATION FOR SEQ ID NO:25:

( i ) SEQUENCE CHARACTERISTICS:
    ( A ) LENGTH: 15 amino acids
    ( B ) TYPE: amino acid
    ( C ) STRANDEDNESS: Not Relevant
    ( D ) TOPOLOGY: linear ( i i ) MOLECULE TYPE: peptide ( x i ) SEQUENCE DESCRIPTION: SEQ ID NO:25:

Trp Gln Thr Val Thr Ile Phe Val Ala Gly Val Leu Thr Ala Ser
1               5                   10                  15

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:26:

Leu Thr Ile Trp Lys Lys Met Gly
1               5

( 2 ) INFORMATION FOR SEQ ID NO:27:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:27:

Glu Leu Phe Gln Gly Gly Pro
1               5

( 2 ) INFORMATION FOR SEQ ID NO:28:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:28:

Asn Trp Gly Arg Leu Val Ala Phe Phe Val Phe Gly Ala
1               5                   10

( 2 ) INFORMATION FOR SEQ ID NO:29:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide
        ( A ) DESCRIPTION: BH1 fragment, bcl- 2

( v ) FRAGMENT TYPE: internal ( x i ) SEQUENCE DESCRIPTION: SEQ ID NO:29:

Glu Leu Phe Arg Asp Gly Val
1               5

( 2 ) INFORMATION FOR SEQ ID NO:30:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:30:

Asn Trp Gly Arg Ile Val Ala Phe Phe Glu Phe Gly Gly
1               5                   10

( 2 ) INFORMATION FOR SEQ ID NO:31:

( i ) SEQUENCE CHARACTERISTICS:
        ( A ) LENGTH: 21 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: internal ( x i ) SEQUENCE DESCRIPTION: SEQ ID NO:31:

Asp Met Phe Ser Asp Gly Asn Phe Asn Trp Gly Arg Val Val Ala Leu
1               5                   10                  15

Phe Tyr Phe Ala Ser
            20

( 2 ) INFORMATION FOR SEQ ID NO:32:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide
        ( A ) DESCRIPTION: BH1 fragment, bcl- x ( v ) FRAGMENT TYPE: internal ( x i ) SEQUENCE DESCRIPTION: SEQ ID NO:32:

Glu Leu Phe Arg Asp Gly Val
1               5

( 2 ) INFORMATION FOR SEQ ID NO:33:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:33:

Asn Trp Gly Arg Ile Val Ala Phe Phe Ser Phe Gly Gly
1               5                   10

( 2 ) INFORMATION FOR SEQ ID NO:34:

( i ) SEQUENCE CHARACTERISTICS:
        ( A ) LENGTH: 21 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:34:

His Val Phe Ser Asp Gly Val Thr Asn Trp Gly Arg Ile Val Thr Leu
1               5                   10                  15

Ile Ser Phe Gly Ala
            20

( 2 ) INFORMATION FOR SEQ ID NO:35:

( i ) SEQUENCE CHARACTERISTICS:
        ( A ) LENGTH: 21 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:35:

```
Lys Glu Phe Glu Asp Gly Ile Ile Asn Trp Gly Arg Ile Val Thr Ile
1               5                   10                  15
Phe Ala Phe Gly Gly
            20
```

( 2 ) INFORMATION FOR SEQ ID NO:36:

( i ) SEQUENCE CHARACTERISTICS:
        ( A ) LENGTH: 21 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:36:

```
Ala Gln Thr Asp Gln Cys Pro Met Ser Tyr Gly Arg Leu Ile Gly Leu
1               5                   10                  15
Ile Ser Phe Gly Gly
            20
```

( 2 ) INFORMATION FOR SEQ ID NO:37:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:37:

```
Asp Trp Ile His Ser Ser Gly Gly Trp Ala Glu Phe Thr Ala Leu Tyr
1               5                   10                  15
```

( 2 ) INFORMATION FOR SEQ ID NO:38:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:38:

```
Thr Trp Ile Gln Asp Asn Gly Gly Trp Asp Ala Phe Val Glu Leu Tyr
1               5                   10                  15
```

( 2 ) INFORMATION FOR SEQ ID NO:39:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:39:

```
Gly Trp Ile Gln Asp Gln Gly Gly Trp Asp Gly Leu Leu Ser Tyr Phe
1               5                   10                  15
```

( 2 ) INFORMATION FOR SEQ ID NO:40:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:40:

```
Pro Trp Ile Gln Glu Asn Gly Gly Trp Asp Thr Phe Val Glu Leu Tyr
1               5                   10                  15
```

( 2 ) INFORMATION FOR SEQ ID NO:41:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:41:

```
Asp Trp Leu Val Lys Gln Arg Gly Trp Asp Gly Phe Val Glu Phe Phe
1               5                   10                  15
```

( 2 ) INFORMATION FOR SEQ ID NO:42:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:42:

```
Glu Trp Ile Arg Gln Asn Gly Gly Trp Glu Asp Gly Phe Ile Lys Lys
1               5                   10                  15
```

( 2 ) INFORMATION FOR SEQ ID NO:43:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:43:

```
Asn Trp Lys Glu His Asn Arg Ser Trp Asp Asp Phe Met Thr Leu Gly
1               5                   10                  15
```

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear (i i) MOLECULE TYPE: peptide (x i) SEQUENCE DESCRIPTION: SEQ ID NO:44:

Thr Gly Ala Val Ala Leu
1               5

(2) INFORMATION FOR SEQ ID NO:45:

(i) SEQUENCE CHARACTERISTICS:
    (A) LENGTH: 5 amino acids
    (B) TYPE: amino acid
    (C) STRANDEDNESS: Not Relevant
    (D) TOPOLOGY: linear (i i) MOLECULE TYPE: peptide (x i) SEQUENCE DESCRIPTION: SEQ ID NO:45:

Gly Ala Leu Val Thr
1           5

(2) INFORMATION FOR SEQ ID NO:46:

(i) SEQUENCE CHARACTERISTICS:
    (A) LENGTH: 4 amino acids
    (B) TYPE: amino acid
    (C) STRANDEDNESS: Not Relevant
    (D) TOPOLOGY: linear (i i) MOLECULE TYPE: peptide (x i) SEQUENCE DESCRIPTION: SEQ ID NO:46:

Val Gly Ala Phe
1

(2) INFORMATION FOR SEQ ID NO:47:

(i) SEQUENCE CHARACTERISTICS:
    (A) LENGTH: 5 amino acids
    (B) TYPE: amino acid
    (C) STRANDEDNESS: Not Relevant
    (D) TOPOLOGY: linear (i i) MOLECULE TYPE: peptide (x i) SEQUENCE DESCRIPTION: SEQ ID NO:47:

Ser Leu Ala Leu Val
1               5

(2) INFORMATION FOR SEQ ID NO:48:

(i) SEQUENCE CHARACTERISTICS:
    (A) LENGTH: 5 amino acids
    (B) TYPE: amino acid
    (C) STRANDEDNESS: Not Relevant
    (D) TOPOLOGY: linear (i i) MOLECULE TYPE: peptide (x i) SEQUENCE DESCRIPTION: SEQ ID NO:48:

Gly Ala Cys Ile Thr
1               5

(2) INFORMATION FOR SEQ ID NO:49:

(i) SEQUENCE CHARACTERISTICS:
    (A) LENGTH: 4 amino acids
    (B) TYPE: amino acid
    (C) STRANDEDNESS: Not Relevant
    (D) TOPOLOGY: linear (ii) MOLECULE TYPE: peptide (xi) SEQUENCE DESCRIPTION: SEQ ID NO:49:

Leu Gly Ala Tyr
1

(2) INFORMATION FOR SEQ ID NO:50:

(i) SEQUENCE CHARACTERISTICS:
(A) LENGTH: 8 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:50:

Trp Phe Leu Thr Gly Met Thr Val
1               5

(2) INFORMATION FOR SEQ ID NO:51:

(i) SEQUENCE CHARACTERISTICS:
(A) LENGTH: 10 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:51:

Ala Gly Val Val Leu Leu Leu Gly Ser Leu
1               5                   10

(2) INFORMATION FOR SEQ ID NO:52:

(i) SEQUENCE CHARACTERISTICS:
(A) LENGTH: 8 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:52:

Ile Leu Ala Thr Val Ala Ala Thr
1               5

(2) INFORMATION FOR SEQ ID NO:53:

(i) SEQUENCE CHARACTERISTICS:
(A) LENGTH: 6 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:53:

Thr Ala Ile Gly Ala Tyr
1               5

What is claimed is:

1. An isolated nucleic acid molecule consisting of SEQ ID NO:1 or SEQ ID NO:2 or a sequence consisting of 85% sequence identity thereto and encoding mammalian B-cell lymphoma-y (bcl-y) protein.

2. The nucleic acid molecule of claim 1 consisting of SEQ ID NO:1.

3. The nucleic acid molecule of claim 1 consisting of SEQ ID NO:2.

4. A vector comprising the nucleic acid molecule of claim 1.

5. A cellular host transformed with the vector of claim 4.

6. A method of preparing a mammalian bcl-y protein comprising:
   (a) obtaining a cellular host transformed with the vector of claim 4;
   (b) cultivating said host under conditions which result in the expression of mammalian bcl-y;
   (c) isolating the mammalian bcl-y protein so expressed.

7. The method of claim 6, wherein said mammalian bcl-y is encoded by a nucleic acid molecule consisting of SEQ ID NO:1.

8. The method of claim 6, wherein said mammalian bcl-y is encoded by a nucleic acid molecule consisting of SEQ ID NO:2.

* * * * *